(12) United States Patent
Blomet et al.

(10) Patent No.: US 10,953,024 B2
(45) Date of Patent: Mar. 23, 2021

(54) USE OF A CREAM THAT PROTECTS AGAINST THE EFFECTS OF AGGRESSIVE CHEMICAL AGENTS IN CONTACT WITH THE SKIN

(71) Applicant: PREVOR INTERNATIONAL, Paris (FR)

(72) Inventors: Joel Blomet, Valmondois (FR); Laurence Mathieu, Talence (FR); Marie-Claude Meyer, Paris (FR)

(73) Assignee: PREVOR INTERNATIONAL, Paris (FR)

( * ) Notice: Subject to any disclaimer, the term of this patent is extended or adjusted under 35 U.S.C. 154(b) by 0 days.

(21) Appl. No.: 14/415,428

(22) PCT Filed: Jul. 17, 2013

(86) PCT No.: PCT/FR2013/051717
§ 371 (c)(1),
(2) Date: Jan. 16, 2015

(87) PCT Pub. No.: WO2014/013194
PCT Pub. Date: Jan. 23, 2014

(65) Prior Publication Data
US 2015/0190357 A1 Jul. 9, 2015

(30) Foreign Application Priority Data
Jul. 18, 2012 (FR) ........................................ 1256939

(51) Int. Cl.
| | | |
|---|---|---|
| *A61K 31/69* | (2006.01) | |
| *A61K 9/00* | (2006.01) | |
| *A61K 47/18* | (2017.01) | |
| *A61K 47/20* | (2006.01) | |
| *A61K 31/198* | (2006.01) | |
| *A61Q 17/00* | (2006.01) | |
| *A61K 31/197* | (2006.01) | |

(52) U.S. Cl.
CPC ............ *A61K 31/69* (2013.01); *A61K 9/0014* (2013.01); *A61K 31/197* (2013.01); *A61K 31/198* (2013.01); *A61K 47/183* (2013.01); *A61K 47/20* (2013.01); *A61Q 17/00* (2013.01); *A61K 2800/51* (2013.01)

(58) Field of Classification Search
CPC .... A61K 31/69; A61K 9/0014; A61K 31/197; A61K 31/198; A61K 47/183; A61K 2800/51; A61Q 17/00
See application file for complete search history.

(56) References Cited

U.S. PATENT DOCUMENTS

| | | | |
|---|---|---|---|
| 5,587,400 A * | 12/1996 | Blomet | A61K 8/26 514/566 |
| 5,763,486 A | 6/1998 | Blomet et al. | |
| 2002/0051797 A1* | 5/2002 | Jezior | A61K 8/8164 424/401 |
| 2002/0128310 A1* | 9/2002 | Johansson | A61Q 17/005 514/510 |

FOREIGN PATENT DOCUMENTS

| | | | | |
|---|---|---|---|---|
| FR | 2 604 900 A1 | | 4/1988 | |
| WO | 01/93858 A2 | | 12/2001 | |
| WO | WO 2001093858 | * | 12/2001 | ........... A61K 31/198 |
| WO | WO2011041680 | * | 4/2011 | ............... A61K 9/20 |

OTHER PUBLICATIONS

WO 2001093858 (English Machine Translation).*
Gawkrodger et al. (Contact Dermatitis, 1995. 32. 257-265).*
Thiram ("Hazardous Substance Fact Sheet", NJ Dept. of Health, Aug. 2010).*
Zhai ("Chapter 17: Barrier Creams/Moisturizers" in Latex Intolerance Basic Science, Epidemiology, and Clinical Management, 2005, p. 165-176).*
Zhai-2 ("Evaluating Efficacy of Barrier Creams: In Vitro and In Vivo Models" Ch. 52 in Dermatotoxicology, Sixth Edition, 2004, pp. 1087-1102).*
International Search Report, dated Aug. 30, 2013, from corresponding PCT application.

* cited by examiner

*Primary Examiner* — Robert H Havlin
(74) *Attorney, Agent, or Firm* — Maier & Maier, PLLC

(57) ABSTRACT

The use of an emulsion for protecting the skin against aggressive chemical agents, wherein this emulsion includes at least one amphoteric chelating agent which includes a complex based on aluminium and on ethylenediaminetetraacetic acid or the trisodium salt thereof, having the general formula $[Al(Y)B_n]^c D_{c'}$ with B being $OH^-$, $BO_2^-$ or $H^+$, Y being a tetracarboxylate which can be protonated four times to form ethylenediaminetetraacetic acid, n being an integer equal to 0, 1, 2 or 3, D being a counterion, preferably $Na^+$, c being an integer equal to 0, 1, 2 or 3 and c' being a relative number having the same absolute value as c.

29 Claims, 2 Drawing Sheets

Figure 1:
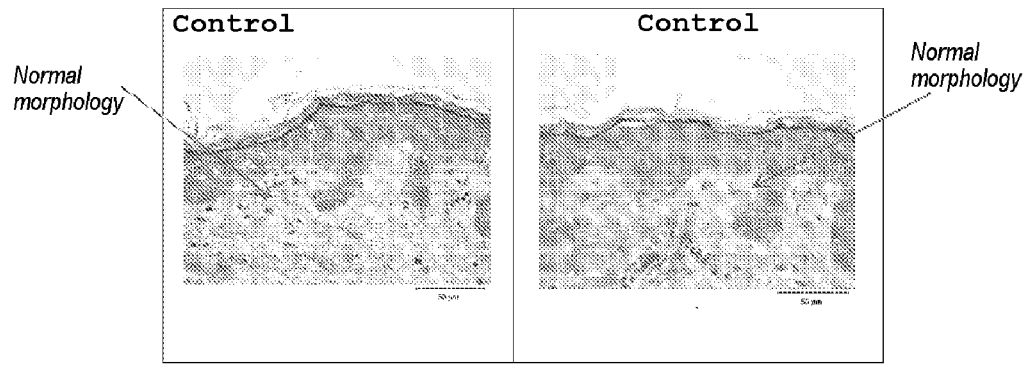

USE OF A CREAM THAT PROTECTS AGAINST THE EFFECTS OF AGGRESSIVE CHEMICAL AGENTS IN CONTACT WITH THE SKIN

FIELD OF THE INVENTION

The present invention relates to the field of products for protecting against aggressive chemical agents that may come into contact with the skin.

CONTEXT OF THE INVENTION

During the handling of aggressive chemicals, notably in factories, laboratories, hair salons, etc., it often happens that accidental splashes of these products come into contact with the skin. From 10% to 15% of occupational diseases are skin diseases, 95% of the latter being contact dermatitides. Occupational contact dermatitis mainly affects the hands. From 0.7 to 1.5 cases per 1000 workers per year were observed.

The frequency of skin irritations is a function both of individual susceptibility and of the frequency and duration of exposure to aggressive chemical agents. Important factors are for example working in a damp environment, with detergents, acids, bases, oxidants, solvents, etc. Moreover, it should be stressed that chronic irritant contact dermatitides also constitute an important risk factor for secondary sensitization.

To reduce the risk of developing occupational dermatoses, wearing of gloves is strongly recommended. However, wearing of the recommended gloves is not always effective for 100% of the working time. In fact, it very often happens that the wearing of gloves is not complied with totally, notably when handling moderately aggressive agents, as the user finds it to be too restrictive by. The people handling aggressive chemicals thus have a tendency to limit the length of time that gloves are worn. Moreover, the effectiveness of protection may only be partial if the material of the glove is not perfectly suitable for the chemical product against which protection is required and/or if the wearing time is prolonged, exceeding the permeation time. Moreover, infiltrations of the aggressive chemicals may occur because of a tear in the glove or because drops of aggressive chemicals may come into contact with the skin via the cuff of the glove or before or after wearing the gloves. Application of a cream that is intended to form a physical barrier against certain specific substances that are slightly aggressive or certain specific allergens makes it possible to protect the skin against these agents notably when the latter come into contact with the skin before or after wearing the gloves.

Over the last three decades, preparation of these protective creams has passed from the empirical stage to the stage of scientific research. Protective formulations for the skin (cream and gel) are based on various topical vehicles (generally oil-in-water or water-in-oil emulsions as well as gels based on cellulose ether or acrylic polymer). However, such formulations are always designed for use in specified environmental conditions, i.e. for protecting against irritants of a specific type.

Thus, creams/gels of this kind are on the market. The problem that arises is that these formulations are intended for protecting the skin only against a narrow spectrum of slightly aggressive water-soluble or oil-soluble agents. This is due to the fact that they work based on a mechanical effect: once it has penetrated, the cream forms a barrier between the skin and the external aggressive agents. This barrier is effective against aggressive agents that are not soluble therein. Thus, the effectiveness of such products is reduced since only solubility is taken into account and not other parameters such as molecular weight, partition coefficient, chemical reactivity, etc. Such products are never universally employed.

At present there is no cream capable of effectively protecting the skin against a broad spectrum of chemicals of all kinds, and notably against allergens.

Surprisingly and unexpectedly, the present inventors have formulated a cream for protecting skin against all types of aggressive chemical agents.

SUMMARY OF THE INVENTION

The present invention relates generally to the use of a cream or emulsion for protecting the skin against aggressive chemical agents, said cream comprising an amphoteric chelating agent. It also relates to said emulsion. In the sense of the present invention, emulsion means an emulsion selected from the group comprising an oil-in-water emulsion, a water-in-oil emulsion, a multiple emulsion, a microemulsion, a nanoemulsion, and mixtures thereof.

More specifically, according to a first aspect, the present invention relates to the use of an emulsion for protecting the skin against aggressive chemical agents, and notably against allergens.

According to a second aspect, the present invention relates to the use of said emulsion for preventing contact dermatitides.

According to a third aspect, the present invention relates to said emulsion.

According to a fourth aspect, the present invention relates to the method of preparing said emulsion.

A more detailed description of certain preferred embodiments of the invention is given below.

DETAILED DESCRIPTION OF THE INVENTION

The present invention relates to the use of an emulsion for protecting the skin against aggressive chemical agents, said emulsion comprising at least one amphoteric chelating agent comprising a complex based on aluminum and deprotonated ethylenediaminetetraacetic acid, having the general formula $[Al(Y)B_n]^{c'}D_c$ with B representing $OH^-$, $BO_2^-$, $H^+$, Y representing a tetracarboxylate that may be protonated four times to form ethylenediaminetetraacetic acid, n representing an integer equal to 0, 1, 2 or 3, D being a counterion, preferably $Na^+$, c being an integer equal to 0, 1, 2 or 3 and c' being a relative number having the same absolute value as c.

This amphoteric chelating agent may be preferably formed by a quasi-stoichiometric combination of aluminum ion $Al^{3+}$, ligand Y and a stabilizer selected from $OH^-$, $BO_2^-$ or $H^+$. In consequence, its pH remains neutral, the lowest of its acid pKs is in the range from 6 to 10 whereas the highest of its basic pKs is in the range from 5 to 8, and the highest basic pK is less than the lowest acid pK.

In the sense of the present invention, cream means an emulsion, i.e. an oil-in-water emulsion, a water-in-oil emulsion, a multiple emulsion, a microemulsion, or a nanoemulsion. These two terms "cream" and "emulsion" can therefore be used interchangeably in the present description.

According to a particular embodiment, said complex based on aluminum and Y is stabilized with a weak base such as amino acids selected from the group comprising glycine, histidine, arginine, lysine, phenylalanine, alanine, isoleucine, leucine, methionine, proline, valine, tryptophan, serine, glutamine, cystine and mixtures thereof. Glycine is particularly suitable.

The amount of amphoteric chelating agent present in said emulsion is from 0.01 to 5%, preferably from 0.1 to 2% and even more preferably from 0.2 to 1% by weight based on the total weight of the emulsion. An amount below 0.01% does not allow an adequate protective effect to be obtained. Above 5%, no appreciable improvement is observed.

According to the invention, the emulsion is used in topical application, more particularly cutaneous application.

Without wishing to be bound to a theory, the present inventors are of the opinion that the emulsion according to the invention makes it possible to form a physical and chemical barrier against aggressive chemical agents. More particularly, after application and drying, a barrier layer devoid of water covers the skin, thus providing a physical barrier between the skin and the external environment, and as for the amphoteric chelating agent, it provides a chemical barrier by chelating or reacting chemically with chemicals that come in contact with this layer of cream.

By this dual action, the aggressive agents are prevented from coming into contact with the skin.

To be effective, the emulsion must completely cover the area of skin to be protected, generally the hands. It must be applied regularly on the entire area, at a rate of about 0.5 to 5 mg/cm$^2$, preferably about 1 to 3 mg/cm$^2$, and even more preferably about 2 mg/cm$^2$.

For optimal effectiveness, it is desirable to apply the product at least 5 minutes, preferably at least 10 minutes and even more preferably at least 15 minutes before contact with aggressive chemical agents.

The protective layer formed on the skin will last for a varying length of time, depending on the activity. In any case, application of the cream according to the invention will have to be renewed after each washing of the hands. In the absence of washing of the hands and without significant and/or repeated mechanical rubbing, the protective layer will be effective for up to 4 hours. If the activity causes a lot or rubbing, it will be advisable to renew application more frequently. Thus, it is recommended to renew application of the emulsion according to the invention at least every 4 hours or after each washing of the hands.

In the sense of the present invention, the aggressive chemical agents include chemical irritants and allergenic products. The chemical irritants comprise substances and mixtures belonging to categories H311, H312, H314, H315, H317 as defined in the CLP regulations (regulation (EC) No. 1272/2008 relating to the classification, labeling and packaging of substances and mixtures). They also include products having a pH from 2 to 11.5.

Thus, in EC regulation No. 1272/2008, the product H311 is defined as toxic by skin contact. Product H312 is defined as harmful by skin contact. Product H314 is defined as causing serious skin burns and eye lesions. Product H315 is defined as causing skin irritation. Product H317 is defined as possibly causing a skin allergy.

The emulsion according to the invention complies with standard NFS75601. This standard relates to protective creams that are applied as a precaution on the skin to provide temporary protection against moderately aggressive products. "Moderately aggressive products" means substances or preparations that are not classified as very toxic, toxic, corrosive or allergenic by the regulations relating to the labeling of hazardous substances. This standard stipulates the characteristics of these protective creams and their limits of use. It does not apply to preparations intended to protect against possible physical or microbiological risks.

The emulsion may be used effectively against chemical irritants that are water-soluble or that are not water-soluble.

As examples of water-soluble irritants, we may mention acids, bases, chlorinated products, etc. More particularly, these products may be selected from the group comprising sodium hydroxide of pH 11.50, hydrochloric acid of pH 2.00, sodium hypochlorite up to 12%, sodium lauryl sulfate in aqueous solution at a concentration that may be up to 5% and mixtures thereof. As examples of irritants that are not water-soluble, we may mention: long-chain hydrocarbon solvents, chlorinated solvents and mixtures thereof. In particular, such products may be selected from the group comprising mineral oil, white spirit (C9-C16 alkane/cycloalkane) and mixtures thereof. We may also mention commonly used products such as detergents, glues, strippers, wood treatment products, agricultural treatment products such as insecticides, pesticides, fertilizers; cements and mortars, products for filling or consolidating rock cavities, dyes. The cream according to the invention is effective against products requiring special labeling on account of their toxicity.

The allergenic products comprise organic substances, particles or bodies (atoms, molecules, proteins, glycoproteins or any other macromolecular organic substance of complex structure), which, in contact with the skin, are capable of causing an allergic reaction in a previously sensitized subject. This allergic reaction may lead to skin damage or even a pathological phenomenon. As examples of allergenic products, we may mention the allergens selected from the group comprising heavy metals (for example: Al, As, Cd, Cr, Hg, Ni, Pb, Sr, Te), tetramethylthiuram disulfide, 2-mercaptobenzothiazole, benzyl carbamate, bisphenol, ethyl acrylate, Araldite 506 epoxy resin, hevein, methanal, allergens of the protein type (such as profilins, tropomyosins, LTPs (lipid transfer proteins), the Bet v 1-like proteins PR-10, polcalcins, beta parvalbumins, 2s albumins, beta expansins, polygalacturonases, Ag5 (antigens 5), albumins, caseins, lipocalin, group 5 grasses, 11s globulins, 7s vicilin-like globulins, group 4 grasses, papain-like cysteine proteases, phospholipases A1, serine protease inhibitors, hyaluronidases, class 1 chitinases, thaumatin-like proteins, etc.) and mixtures thereof.

The effectiveness of use of the emulsion according to the invention was tested by morphological analyses.

To prove effectiveness against irritants, two methodologies were employed: analyses of morphology and studies allowing assay of interleukins and notably of IL-6 and IL-8.

Analysis of cellular morphology was performed by staining with Masson's trichrome, Goldner variant. The presence of morphological changes indicates that the test substance has caused severe irritation, which has thus altered the cellular structure. After application of the oil-in-water emulsion according to the invention, no morphological change was observed after the area of skin covered with the emulsion was brought in contact with the following aggressive chemical agents: sodium hydroxide at pH 11.50, hydrochloric acid at pH 2.00, sodium hypochlorite at 12%, sodium lauryl sulfate at 5%, mineral oil and white spirit (C9-C16 alkane/cycloalkane).

Effectiveness was also demonstrated in experiments with assay of interleukins. The concentration of interleukin IL-6 (produced first) and IL-8 (produced second) in the dermis is a function of the process of inflammation of the skin. After application of the emulsion on the skin, no appreciable increase in content of interleukin 6 or 8 was observed after the area of skin covered with the emulsion was brought into contact with the following agents: sodium hydroxide at pH 11.50, hydrochloric acid at pH 2.00, sodium hypochlorite at 12%, sodium lauryl sulfate at 5%, mineral oil, and white spirit (C9-C16 alkane/cycloalkane).

Effectiveness of use of the amphoteric chelating agent according to the invention was tested by morphological analyses based on the following theory: The Langerhans cells are dendritic cells that are present in the epidermis and contain Birbeck granules. They are normally present in lymph nodes and in the skin at the level of the stratum spinosum of the epidermis. These specialized cells for capture of antigens are activated when the skin comes in contact with an allergen. This gives a first sign of the initiation of a sensitization process. Methods of immunolabeling, notably of the CD1a surface receptors of the Langerhans cells, make it possible to measure their number and observe their migration from the epidermis to the dermis. The prophylactic composition of the invention is effective if the antigen is stopped, i.e. not captured by the epidermal Langerhans cells. Therefore the latter will not migrate to the dermis. The effectiveness of the composition according to the invention is therefore measured by the number of Langerhans cells not migrating per centimeter of epidermis. No appreciable migration of the number of these cells was observed after the area of skin covered with the emulsion was brought into contact with heavy metals (for example: Al, As, Cd, Cr, Hg, Ni, Pb, Sr, Te), tetramethylthiuram disulfide, 2-mercaptobenzothiazole, benzyl carbamate, bisphenol, ethyl acrylate, Araldite 506 epoxy resin, hevein and methanal.

According to another aspect, the present invention relates to an emulsion for use in the prevention of contact dermatitis.

Contact dermatitis is a skin reaction resulting from prolonged or repeated exposure to allergenic or irritant substances. A distinction is made between irritant contact dermatitis (ICD) and allergic contact dermatitis (ACD).

Among the allergic contact dermatitides, a distinction is made between: reactions of the immediate type: contact urticaria, and reactions of the delayed type: eczema.

Moreover, the irritant dermatitides may display an acute or chronic character.

"Contact dermatitis" in the sense of the invention means all these types of skin reactions.

The emulsion according to the invention prevents direct contact of the skin with said agents and thus helps to avoid contact dermatitis by construction of a physical barrier by forming a film devoid of water as well as a chemical barrier using both the properties of amphoteric chelating agent and the reactive properties of the cream according to the invention.

Thus, the emulsion allows prevention of contact dermatitides caused by certain chemicals or even by the wearing of protective gloves.

The emulsion according to the invention may be applied daily. The conditions of use are identical to those described above.

The embodiments described below relate both to the emulsion as such and to the use of said emulsion.

According to a particular embodiment, said emulsion is an oil-in-water emulsion.

The emulsion comprises an aqueous phase, an oily phase and at least one surfactant.

The surfactant may be hydrophobic with an HLB from 3 to 10 (for emulsions that are not oil-in-water) or hydrophilic with an HLB from 11 to 18. This surfactant is selected from the group comprising ethoxylated fatty alcohols, fatty acids and esters (for example: ceteareth-12, ceteareth-20, ceteareth-33, stearyl cetyl alcohol 20-ethoxylated, polyglyceryl 2-polyhydroxystearate, glyceryl oleate, sorbitan ester, glycerol ester, PEG-mono/dilaurate, PEG-mono/distearate, cetearyl isononanoate, glyceryl stearate, etc.), carboxylates, ethoxycarboxylates (for example: sodium/potassium stearate, alkyl-carboxylic acid, alkyl-polyglycol ether carboxylic acid, polyglycol alkylphenol ether carboxylic acid, carboxymethylated alcohol, ethoxycarboxylate, ethercarboxylate, etc.) and mixtures thereof.

The amount of surfactant is from 0.1 to 10 wt %, preferably from 0.5 to 5 wt %, and even more preferably from 1 to 3 wt % based on the total weight of the emulsion.

The oily phase comprises synthetic or natural waxes or oils, selected from the group comprising carnauba extract, beeswax, shea butter, triglycerides, stearins, esters of fatty acids (for example: cetearyl alcohols, dicaprylic ethers of cetyl palmitate, dicaprylic carbonates, cetearyl isononanoates, distearyl-tricarbonate dimers, etc.), silicone oils, zinc stearates, polyisobutenes, octyldodecanols, octyldecyl xylosides, fatty alcohols, fatty acids (for example: lauric acid, myristic acid, stearic acid, etc.), vegetable oils (for example: sunflower oil, jojoba oil, coconut oil, soybean oil, almond oil, etc.) and mixtures thereof.

The oily phase represents up to 98 wt %, notably up to 70 wt %, preferably 5 to 50 wt %, and even more preferably from 10 to 20 wt % based on the total weight of the emulsion.

The aqueous phase comprises essentially water, preferably purified water. It is present at a level from 1 to 90 wt %, preferably from 30 to 80 wt %, and even more preferably from 50 to 70 wt % based on the total weight of the emulsion.

The emulsion according to the invention may include various agents conferring advantageous properties for the skin. These agents are present either in the aqueous phase or in the oily phase, depending on their solubility.

These agents are notably hydrating agents, emollients, antiperspirants, etc.

The hydrating agents and emollients may be selected from the group comprising allantoin, polyol (for example glycerol, glycerol polymers, propylene glycol, sorbitol etc.), vegetable extracts (for example extracts of aloe vera, of chamomile, of cucumber, of calendula, etc.), hyaluronic acid, pyrrolidone carboxylic acid, urea, chitosan, tocopherol, panthenol, butylene glycol, phospholipid, linoleic acid, γ-linoleic acid, alpha-bisabolol, and mixtures thereof.

The concentration of hydrating agents and emollients is from 0.1 to 20 wt %, preferably from 0.5 to 10 wt %, and even more preferably from 1 to 5 wt % based on the total weight of the emulsion.

The antiperspirants may be selected from the group comprising aluminum salts, preferably aluminum sesquihydrochloride, salts of aluminum and zirconium, aluminum-zirconium octachlorohydrex glycine complexes and mixtures thereof. The concentration of antiperspirant is from 0.1 to 50 wt %, preferably from 10 to 30 wt %, and even more preferably 15 wt % based on the total weight of the emulsion.

The emulsion may also comprise additives for improving texture such as conditioners and thickeners.

The conditioners may be selected from the group comprising polycationic polymers denoted according to the INCI nomenclature as polyquaterniums, quaternized gums, quaternized phospholipids, and mixtures thereof. The concentration of conditioner is from 0.1 to 20 wt %, preferably from 0.5 to 10 wt %, and even more preferably from 0.5 to 5 wt % based on the total weight of the emulsion.

The thickeners may be selected from the group comprising: polymers and copolymers of acrylic acid, $C_{10-30}$ alkyl acrylate/acrylate crosslinked polymers, polyacrylamide, poloxamer, cellulose derivatives (esters and ethers), silicas, fumed silica, silicates, such as magnesium-aluminum silicates, chitin and derivatives thereof, gelatin, xanthan, dextran, gellan, carrageenans, alginates, agar-agar, agar, pectin, acacia gum, karaya gum, tragacanth gum, gum arabic, guar gum, carob gum, starch and derivatives thereof, scleroglucan and mixtures thereof. The concentration of thickener is from 0.01 to 10 wt %, preferably from 0.1 to 5 wt %, and even more preferably from 0.5 to 3 wt % based on the total weight of the emulsion.

The emulsion may also comprise preservatives. The latter may be selected from the group comprising: para-hydroxybenzoic ester, isothiazolinone, imidazolidinyl urea, diazolidinyl urea, bromo-nitro-propanediol, phenoxyethanol, sorbic acid and salts thereof, benzoic acid and salts thereof, phenoxyethanol, benzyl alcohol, and mixtures thereof. The concentration is that permitted in cosmetics.

Finally, the formulation may comprise cosmetic and food colorants, perfumes, aromas, pH regulators (for example, citric acid, lactic acid, phosphoric acid, sodium hydroxide, potassium hydroxide, aminomethyl-propanol, triethanolamine, etc.) and mixtures thereof. Their concentration may be from 0.1 to 50 wt %, preferably from 10 to 30 wt %, and even more preferably 15 wt % based on the total weight of the emulsion.

According to another aspect, the present invention relates to the method of preparing said emulsion.

Said emulsion may be prepared by any technique known by a person skilled in the art. However, in order to optimize its stability, it is best to prepare the aqueous phase first, incorporating therein the amphoteric chelating agent by mixing cold, and then incorporate this preparation in the oily phase before mixing for the purpose of emulsification.

In a second embodiment, it is best to prepare the aqueous phase, incorporating therein the amphoteric chelating agent by mixing hot, and then incorporate this preparation in the oily phase before mixing for the purpose of emulsification.

Hot mixing may be done at 50-90° C., preferably at 60-80° C. and even more preferably at 70° C.

In the sense of the present invention, it is considered that the stability is satisfactory if no phase separation is observed after storage of the emulsion at room temperature for 6 months, preferably for 1 year.

The present invention will be described in more detail based on the following examples.

EXAMPLES

The following examples describe certain embodiments of the present invention. However, it is to be understood that the examples are only presented for purposes of illustration and do not in any way limit the scope of the invention.

In the present examples, the amphoteric chelating agent used has the following formula: $[AlYBO_2]^{2-}Na^+_2$.

Example 1: Emulsion for External Use

An emulsion comprising the following products was prepared:

| | |
|---|---|
| Glycerol stearate/cetearyl alcohol/cetyl palmitate/coconut glycerides (weight ratio: 60%/20%/10%/10%) | 0.12 g |
| Ethoxylated cetearyl alcohol (12 mol) | 0.01 g |
| Ethoxylated cetearyl alcohol (20 mol) | 0.02 g |
| C18-caprylate/caprate | 0.09 g |
| Caprylic/capric triglyceride | 0.03 g |
| Liquid paraffin | 0.02 g |
| Propylparaben/paraben benzoate (50/50 w/w) | 0.004 g |
| Purified water | q.s. 1 g |
| Glycerin | 0.03 g |
| Amphoteric chelating agent | 0.002 g |

This oil-in-water emulsion has the following characteristics:

Brookfield viscosity of 18000 cP, measured at a temperature of 20(+/−1)° C. and at a spindle speed of 3/20 rpm, pH of 6.45, No phase separation occurred after storage for 6 months at room temperature.

Example 2: Emulsion for External Use

In the same way as in example 1, an emulsion was prepared containing:

| | |
|---|---|
| Glycerol stearate/cetearyl alcohol/cetyl palmitate/coconut glycerides (weight ratio 60%/20%/10%/10%) | 0.12 g |
| Ethoxylated cetearyl alcohol (12 mol) | 0.011 g |
| Ethoxylated cetearyl alcohol (20 mol) | 0.022 g |
| C18-caprylate/caprate | 0.08 g |
| Caprylic/capric triglyceride | 0.04 g |
| Dicaprylyl ether | 0.03 g |
| Liquid paraffin | 0.025 g |
| Zinc oxide | 0.01 g |
| Propylparaben, benzoate paraben (50/50 w/w) | 0.004 g |
| Purified water | q.s. 1 g |
| Glycerin | 0.03 g |
| Citric acid | 0.001 g |
| Aluminum/magnesium silicate | 0.007 g |
| Amphoteric chelating agent | 0.002 g |

This oil-in-water emulsion has the following characteristics:

Brookfield viscosity of 21000 cP, measured at a temperature of 20(+/−1) ° C. and at a spindle speed of 3/20 rpm pH of 6.55

No phase separation occurred after storage for 6 months at room temperature.

Example 3: Emulsion for External Use

In the same way as in example 1, an emulsion was prepared containing:

| | |
|---|---|
| Cetearyl alcohol/sodium cetearyl sulfate/sodium lauryl sulfate (weight ratio: 60%/35%/5%) | 0.05 g |
| Dicaprylyl carbonate | 0.011 g |
| Propylparaben/benzoate paraben (50%/50% w/w) | 0.004 g |
| Purified water | q.s. 1 g |
| Glycerin | 0.01 g |
| Kaolinite | 0.1 g |
| Xanthan gum | 0.01 g |
| Amphoteric chelating agent | 0.002 g |

This oil-in-water emulsion has the following characteristics:
Brookfield viscosity of 14500 cP, measured at a temperature of 20(+/−1) ° C. and at a spindle speed of 3/20 rpm
pH of 6.80
No phase separation occurred after storage for 6 months at room temperature.

Example 4: Emulsion for External Use

In the same way as in example 1, an emulsion was prepared containing:

| | |
|---|---|
| Purified water | q.s. 1 g |
| isononyl isononanoate | 0.045 g |
| Octyl dodecanol and octyldodecyl xyloside and PEG-30 Dipolyhydroxystearate | 0.025 g |
| Polyacrylate-13 and Polyisobutylene and polysorbate-20 | 0.01 g |
| Glycerin | 0.03 g |
| Aluminum sesquihydrochloride | 0.15 g |
| Benzoate sodium (and) potassium sorbate | 0.0045 g |
| Amphoteric chelating agent | 0.002 g |

This oil-in-water emulsion has the following characteristics:
Brookfield viscosity of 12000 cP, measured at a temperature of 20(+/−1) ° C. and at a spindle speed of 3/20 rpm
pH of 4.30
No phase separation occurred after storage for 6 months at room temperature.

Example 5: Test of Effectiveness Against Irritants

Skin explants are prepared with an average diameter of 10 mm, derived from abdoplasty of a Caucasian woman of 49 years. These explants are kept alive in a BEM (BIO-EC explant Medium) culture medium at 37° C. in a humid atmosphere enriched with 5% $CO_2$.
The effectiveness of the cream is tested against the following irritants:
Irritants in Aqueous Solution:
sodium hydroxide at pH 11.50—Ref: S/4945/PB15 Fisher Chemical;
hydrochloric acid at pH 2.00—Ref: H/1000/PB18 Fisher Chemical;
sodium hypochlorite at 12%—Ref: 27895 Prolabo;
sodium lauryl sulfate at 5% w/w—Cognis
Oil-Soluble Irritants:
mineral oil—Liquid Paraffin Codex Interchimie;
white spirit (C9-C16 alkane/cycloalkane)—Shellsol D60, Shell.
At $T_0$, the cream from example 1 above is applied on the skin explants at a dosage of 3 mg/cm². It is left to dry for 15 min. Then 25 µl of a solution of an irritant selected from the above list is applied on the protected skin explants (test) and is also applied on unprotected skin explants (control). It is left to stand until $T_{4h}$, which represents 4 hours of exposure to the irritants.
In parallel, explants protected by the cream but which are not brought into contact with a test substance (control) are prepared in the same way.
The effectiveness of protection against irritants is measured by analysis of cellular morphology after staining with Masson's trichrome, Goldner variant. The presence of morphological changes indicates that the test substance has caused severe irritation, which has thus altered the structure of the cells.

Figure 2:
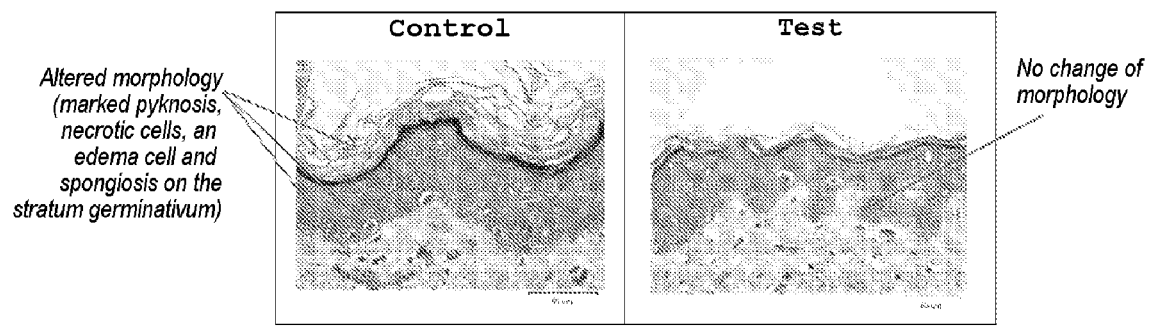

Samples are taken for all the explants at $T_0$ and at $T_{4h}$ and are photographed.
The results are shown in FIGS. 1 and 2 for the solution of sodium hydroxide at pH 11.5(+/−0.1). FIG. 1 shows the explants at $T_0$ and FIG. 2 at $T_{4h}$.
At $T_0$, the stratum corneum is fine, moderately compact and moderately keratinized at the surface, a little more at depth.
The epidermis has from 4 to 5 cellular layers with good morphology and slight spongiosis in the basal layers. The outline of the junction between dermis and epidermis is clear. The papillary dermis has a dense network of fairly thick collagen fibers. It comprises many cells and does not comprise a zone of apparent histological lysis.
At $T_{4h}$ the epidermis of the unprotected explants has 4-5 cellular layers with definite morphological changes. These changes are characterized by considerable cytoplasmic denaturation, nuclear pyknosis and definite spongiosis in the stratum germinativum.
However, the protected explants ("test") and "control" do not show any significant histological change.
Entirely similar results are observed with the other irritants tested.
The absence or the low level of cellular change as well as the low concentration of interleukins have demonstrated that the oil-in-water emulsion from example 1 protects the skin effectively against the irritants tested.

Example 6: Test of Effectiveness Against Allergens

Explants are prepared as described in example 5 above.
The effectiveness of the cream is tested against the following allergens:
heavy metals (Al, As, Cd, Cr, Hg, Ni, Pb, Sr, Te)—ECP multi-element standard V Ref 0C467028 Merck;
Tetramethylthiuram disulfide—T2 420;
2-Mercaptobenzothiazole—M3301;
Benzyl carbamate—B18200;
Bisphenol—13302;
Ethyl acrylate—W241806;
Araldite 506 epoxy resin—A3183;
Hevein—latex 4335932;
Methanal at 30% w/w—116 99031.
At $T_0$, the cream from example 2 above is applied on the skin explants at a dosage of 3 mg/cm². It is left to dry for 15 min. Then 25 µl of a solution of one of the allergens selected from the above list is applied on the skin explants protected by the cream (test) and is also applied on unprotected skin explants (blank). It is left to stand until $T_{4h}$, which represents 4 hours of exposure to the allergens without washing or abrasive rubbing.
In parallel, explants protected by the cream but which are not brought into contact with a test substance (control) are prepared in the same way.
The effectiveness of protection against allergens is measured by immunostain analysis of the CD1a receptors of the Langerhans cells. Firstly, the paraffin-embedded sections of Langerhans cells are immunostained with anti-CD1a monoclonal antibodies (ref. IM1590, clone O10, Beckman Coulter) for 1 hour at room temperature. This immunostaining is reinforced with a streptavidin/biotin system (Vector, PK-7200) and developed using VIP (Vector, SK-4600). The nuclei are counterstained with Masson's hemalum. The Langerhans cells are counted on each section along the epidermis. The length of each section is measured with the Olympus Cell software and the average number of Langerhans cells per centimeter of epidermis is calculated.

The effectiveness of protection against allergens is measured by immunostain analysis of CD1a. Firstly, the paraffin-embedded sections of Langerhans cells are immunostained with anti-CD1a monoclonal antibodies (ref. IM1590, clone O10, Beckman Coulter) for 1 hour at room temperature. This immunostaining is reinforced by a streptavidin/biotin system (Vector, PK-7200) and developed using VIP (Vector, SK-4600). The nuclei are counterstained with Masson's hemalum. The Langerhans cells are counted on each section along the epidermis. The length of each section is measured with the Olympus Cell software and the average number of Langerhans cells per centimeter of epidermis is calculated.

The effectiveness of protection against the allergen is measured by the number of Langerhans cells that have not migrated.

Samples are taken for all the explants at $T_0$ and at $T_{4h}$ and are microphotographed.

Figure 3:
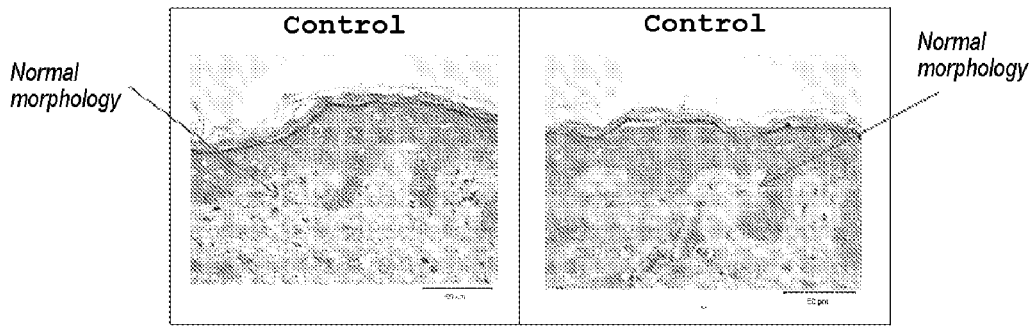
Figure 4:
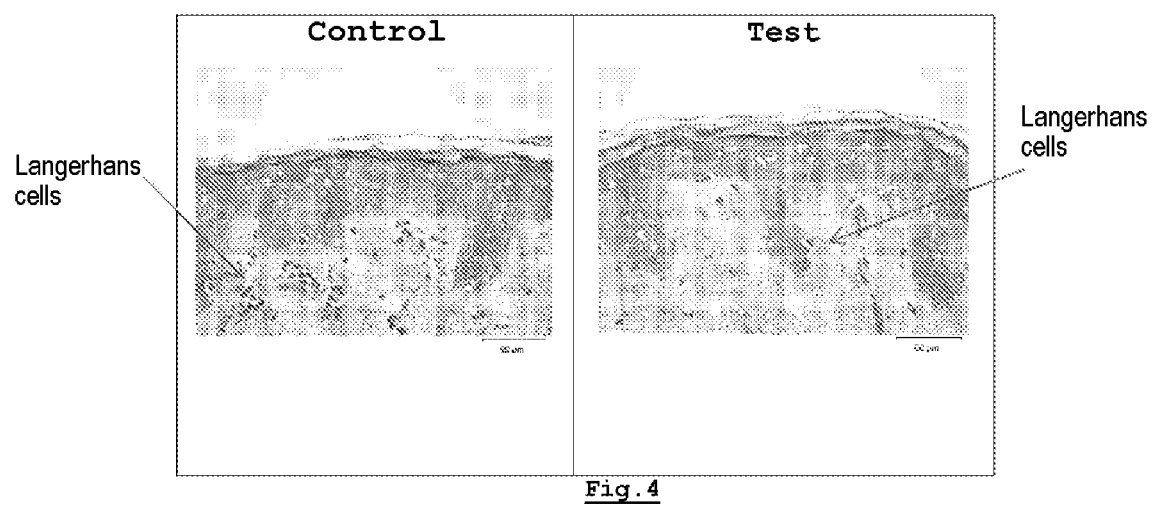

The results are presented in FIGS. 3 and 4. FIG. 3 shows the explants at $T_0$ and FIG. 4 at $T_{4h}$ for hevein.

At $T_0$, the stratum corneum is fine, compact and moderately filled with keratin at the surface and remarkably lower down. The epidermis has from 4 to 5 cellular layers with good morphology and a slight spongiosis on the stratum germinativum. The outline of the junction between the dermis and the epidermis is pronounced. The papillary dermis has fairly thick fibers forming a dense network and it comprises many cells and does not comprise a zone of apparent histological lysis.

The epidermis of the unprotected explants has 4-5 cellular layers with remarkable morphological changes. These changes are characterized by a marked cytoplasmic denaturation (protein degradation), pronounced pyknosis and pronounced spongiosis on the stratum germinativum.

However, the protected and "control" explants do not show any significant histological change.

Similar results were obtained with each of the other allergens tested.

The absence or low level of cellular change as well as the low concentration of interleukins demonstrated that the cream from example 2 protects the skin effectively against the allergens tested.

The invention claimed is:

1. A method for protecting the skin against aggressive chemical agents, comprising applying to the skin an emulsion comprising at least one amphoteric chelating agent that comprises a complex based on aluminum and ethylenediaminetetraacetic acid or its trisodium salt having the formula $[Al(Y)BO_2^-]^{2-}Na^{2+}$ with Y representing a tetracarboxylate, which may be protonated four times to form ethylenediaminetetraacetic acid, the emulsion being applied to the skin at least five minutes before contact with said aggressive chemical agent, thereby providing a physical barrier and a chemical barrier between the skin and said aggressive chemical agent, said amphoteric chelating agent being stabilized with an amino acid selected from the group consisting of histidine, arginine, phenylalanine, isoleucine, leucine, methionine, proline, valine, tryptophan, serine, glutamine, cystine and mixtures thereof, and exposing the skin to which the emulsion has been applied to the aggressive chemical agent, wherein the aggressive chemical agent is an allergen selected from the group consisting of tetramethylthiuram disulfide, 2-mercaptobenzothiazole, benzyl carbamate, bisphenol, ethyl acrylate, Araldite 506 epoxy resin, hevein, methanal and mixtures thereof.

2. A method for protecting the skin against aggressive chemical agents, comprising applying to the skin an emulsion comprising at least one amphoteric chelating agent that comprises a complex based on aluminum and ethylenediaminetetraacetic acid or its trisodium salt having the formula $[Al(Y)BO_2^-]^{2-}Na^{2+}$ with Y representing a tetracarboxylate, which may be protonated four times to form ethylenediaminetetraacetic acid, the emulsion being applied to the skin at least five minutes before contact with said aggressive chemical agent, thereby providing a physical barrier and a chemical barrier between the skin and said aggressive chemical agent, said amphoteric chelating agent being stabilized with an amino acid selected from the group consisting of histidine, arginine, phenylalanine, isoleucine, leucine, methionine, proline, valine, tryptophan, serine, glutamine, cystine and mixtures thereof, and exposing the skin to which the emulsion has been applied to the aggressive chemical agent, wherein the aggressive chemical agent is an allergen selected from the group consisting of Al, As, Cd, Cr, Hg, Ni, Pb, Sr, Te, and mixtures thereof.

3. A method for preventing irritant contact dermititides and allergic contact dermititides of the delayed reaction type caused by an aggressive chemical agent, comprising applying to the skin an emulsion before contact with said aggressive chemical agent, thereby providing a physical barrier and a chemical barrier between the skin and said aggressive agent, the emulsion comprising at least one amphoteric chelating agent that comprises a complex based on aluminum and ethylenediaminetetraacetic acid or its trisodium salt having the general formula $[Al(Y)BO_2^-]^{2-}Na^{2+}$ with Y representing a tetracarboxylate, which may be protonated four times to form ethylenediaminetetraacetic acid, said amphoteric chelating agent being stabilized with an amino acid selected from the group consisting of histidine, arginine, phenylalanine, isoleucine, leucine, methionine, proline, valine, tryptophan, serine, glutamine, cystine and mixtures thereof, and exposing the skin to which the emulsion has been applied to the aggressive chemical agent, wherein the aggressive chemical agent is an allergen selected from the group consisting of tetramethylthiuram disulfide, 2-mercaptobenzothiazole, benzyl carbamate, bisphenol, ethyl acrylate, Araldite 506 epoxy resin, hevein, methanal and mixtures thereof.

4. The method of claim 1, wherein the emulsion is applied evenly on an entire area in an amount of about 0.5 to 5 mg/cm$^2$.

5. The method according to claim 1, wherein the emulsion is applied at least 10 minutes before contact with an aggressive chemical agent.

6. The method according to claim 1, wherein the application of the emulsion is renewed at most every 4 hours, or at each washing of the hands.

7. The method of claim 1, wherein the concentration of the amphoteric chelating agent is from 0.01 to 5 wt % based on total weight of the emulsion.

8. The method of claim 1, wherein the emulsion comprises at least one surfactant, the surfactant being hydrophobic with an HLB from 3 to 10 or hydrophilic with an HLB from 11 to 18.

9. The method of claim 8, wherein the concentration of surfactant is from 0.1 to 10 wt %, based on total weight of the emulsion.

10. The method according to claim 1, wherein said emulsion is an oil-in-water emulsion.

11. The method of claim 3, wherein the emulsion is applied evenly on an entire area in an amount of about 0.5 to 5 mg/cm$^2$.

12. The method of claim 3, wherein the emulsion comprises at least one surfactant, the surfactant being hydrophobic with an HLB from 3 to 10 or hydrophilic with an HLB from 11 to 18.

13. The method according to claim 3, wherein said emulsion is an oil-in-water emulsion.

14. The method of claim 1, wherein the emulsion is applied evenly on an entire area in an amount of about 1 to 3 mg/cm$^2$.

15. The method according to claim 1, wherein the emulsion is applied at least 15 minutes before contact with an aggressive chemical agent.

16. The method of claim 3, wherein the emulsion is applied evenly on an entire area in an amount of about 1 to 3 mg/cm$^2$.

17. A method for preventing irritant contact dermititides and allergic contact dermititides of the delayed reaction type caused by an aggressive chemical agent, comprising applying to the skin an emulsion before contact with said aggressive chemical agent, thereby providing a physical barrier and a chemical barrier between the skin and said aggressive agent, the emulsion comprising at least one amphoteric chelating agent that comprises a complex based on aluminum and ethylenediaminetetraacetic acid or its trisodium salt having the general formula $[Al(Y)BO_2^-]^{2-}Na^{2+}$ with Y representing a tetracarboxylate, which may be protonated four times to form ethylenediaminetetraacetic acid, said amphoteric chelating agent being stabilized with an amino acid selected from the group consisting of histidine, arginine, phenylalanine, isoleucine, leucine, methionine, proline, valine, tryptophan, serine, glutamine, cystine and mixtures thereof, and exposing the skin to which the emulsion has been applied to the aggressive chemical agent, wherein the aggressive chemical agent is an allergen selected from the group consisting of Al, As, Cd, Cr, Hg, Ni, Pb, Sr, Te, and mixtures thereof.

18. A method for protecting the skin against aggressive chemical agents, comprising applying to the skin an emulsion before contact with said aggressive chemical agents to provide a physical barrier and a chemical barrier between the skin and said aggressive chemical agents, said emulsion comprising at least one amphoteric chelating agent that comprises a complex based on aluminum and ethylenediaminetetraacetic acid or its trisodium salt having the general formula $[Al(Y)BO_2^-]^{2-}Na^{2+}$ with Y representing a tetracarboxylate, which may be protonated four times to form ethylenediaminetetraacetic acid, wherein the emulsion comprises at least one surfactant, the surfactant being hydrophobic with an HLB from 3 to 10 or hydrophilic with an HLB from 11 to 18, and exposing the skin to which the emulsion has been applied to the aggressive chemical agent, wherein the aggressive chemical agent is an allergen selected from the group consisting of tetramethylthiuram disulfide, 2-mercaptobenzothiazole, benzyl carbamate, bisphenol, ethyl acrylate, Araldite 506 epoxy resin, hevein, methanal and mixtures thereof.

19. A method for protecting the skin against aggressive chemical agents, comprising applying to the skin an emulsion comprising at least one amphoteric chelating agent that comprises a complex based on aluminum and ethylenediaminetetraacetic acid or its trisodium salt having the formula $[Al(Y)BO_2^-]^{2-}Na^{2+}$ with Y representing a tetracarboxylate, which may be protonated four times to form ethylenediaminetetraacetic acid, the emulsion being applied to the skin at least five minutes before contact with said aggressive chemical agent, thereby providing a physical barrier and a chemical barrier between the skin and said aggressive agent, wherein the emulsion comprises at least one surfactant, the surfactant being hydrophobic with an HLB from 3 to 10 or hydrophilic with an HLB from 11 to 18, and exposing the skin to which the emulsion has been applied to the aggressive chemical agent, wherein the aggressive chemical agent is an allergen selected from the group consisting of Al, As, Cd, Cr, Hg, Ni, Pb, Sr, Te, and mixtures thereof.

20. A method for preventing irritant contact dermititides and allergic contact dermititides of the delayed reaction type caused by an aggressive chemical agent, comprising applying to the skin an emulsion before contact with said aggressive chemical agent, thereby providing a physical barrier and a chemical barrier between the skin and said aggressive agent, the emulsion comprising at least one amphoteric chelating agent that comprises a complex based on aluminum and ethylenediaminetetraacetic acid or its trisodium salt having the general formula $[Al(Y)BO_2^-]^{2-}Na^{2+}$ with Y representing a tetracarboxylate, which may be protonated four times to form ethylenediaminetetraacetic acid, wherein the emulsion comprises at least one surfactant, the surfactant being hydrophobic with an HLB from 3 to 10 or hydrophilic with an HLB from 11 to 18, and exposing the skin to which the emulsion has been applied to the aggressive chemical agent, wherein the aggressive chemical agent is an allergen selected from the group consisting of tetramethylthiuram disulfide, 2-mercaptobenzothiazole, benzyl carbamate, bisphenol, ethyl acrylate, Araldite 506 epoxy resin, hevein, methanal and mixtures thereof.

21. A method for preventing irritant contact dermititides and allergic contact dermititides of the delayed reaction type caused by an aggressive chemical agent, comprising applying to the skin an emulsion before contact with said aggressive chemical agent, thereby providing a physical barrier and a chemical barrier between the skin and said aggressive agent, the emulsion comprising at least one amphoteric chelating agent that comprises a complex based on aluminum and ethylenediaminetetraacetic acid or its trisodium salt having the general formula $[Al(Y)BO_2^-]^{2-}Na^{2+}$ with Y representing a tetracarboxylate, which may be protonated four times to form ethylenediaminetetraacetic acid, wherein the emulsion comprises at least one surfactant, the surfactant being hydrophobic with an HLB from 3 to 10 or hydrophilic with an HLB from 11 to 18, and exposing the skin to which the emulsion has been applied to the aggressive chemical agent, wherein the aggressive chemical agent is an allergen selected from the group consisting of Al, As, Cd, Cr, Hg, Ni, Pb, Sr, Te, and mixtures thereof.

22. The method according to claim 1, wherein the emulsion is applied to the hands so as to completely cover the hands.

23. The method according to claim 2, wherein the emulsion is applied to the hands so as to completely cover the hands.

24. The method according to claim 3, wherein the emulsion is applied to the hands so as to completely cover the hands.

25. The method according to claim 17, wherein the emulsion is applied to the hands so as to completely cover the hands.

26. The method according to claim 18, wherein the emulsion is applied to the hands so as to completely cover the hands.

27. The method according to claim 19, wherein the emulsion is applied to the hands so as to completely cover the hands.

28. The method according to claim 20, wherein the emulsion is applied to the hands so as to completely cover the hands.

29. The method according to claim 21, wherein the emulsion is applied to the hands so as to completely cover the hands.

* * * * *